US00PP28801P3

(12) United States Plant Patent
Rebello

(10) Patent No.: US PP28,801 P3
(45) Date of Patent: Dec. 26, 2017

(54) ***ARCTOTIS* PLANT NAMED 'BONARC 1116'**

(50) Latin Name: *Arctotis hybrida*
Varietal Denomination: Bonarc 1116

(71) Applicant: Shaun Rebello, Blair Athol (AU)

(72) Inventor: Shaun Rebello, Blair Athol (AU)

(73) Assignee: Bouza Botanicals Pty. Ltd., Yellow Rock, NSW (AU)

( * ) Notice: Subject to any disclaimer, the term of this patent is extended or adjusted under 35 U.S.C. 154(b) by 37 days.

(21) Appl. No.: 14/999,330

(22) Filed: Apr. 25, 2016

(65) Prior Publication Data

US 2017/0311508 P1 Oct. 26, 2017

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — C. A. Whealy

(57) ABSTRACT

A new and distinct cultivar of *Arctotis* plant named 'Bonarc 1116', characterized by its compact and semi-upright plant habit; freely branching growth habit; relatively small leaves; freely flowering habit; single-type inflorescences with dark pink-colored ray florets; and good garden performance.

1 Drawing Sheet

Botanical designation: *Arctotis hybrida.*
Cultivar denomination: 'BONARC 1116'.

BACKGROUND OF THE INVENTION

The present invention relates to a new and distinct *Arctotis* plant, botanically known as *Arctotis hybrida* and hereinafter referred to by the name 'Bonarc 1116'.

The new *Arctotis* plant is a product of a planned breeding program conducted by the Inventor in Yellow Rock, New South Wales, Australia. The objective of the breeding program is to create new compact and freely branching *Arctotis* plants that flower early and have attractive ray floret coloration.

The new *Arctotis* plant originated from a cross-pollination conducted by the Inventor in June, 2010 in Yellow Rock, New South Wales, Australia of a proprietary selection of *Arctotis hybrida* identified as code number 09-74, not patented, as the female, or seed, parent with a proprietary selection of *Arctotis hybrida* identified as code number 09-1, not patented, as the male, or pollen, parent. The new *Arctotis* plant was discovered and selected by the Inventor as a single flowering plant within the progeny of the stated cross-pollination in a controlled greenhouse environment in Yellow Rock, New South Wales, Australia on Aug. 11, 2011.

Asexual reproduction of the new *Arctotis* plant by vegetative tip cuttings in a controlled greenhouse environment in Yellow Rock, New South Wales, Australia since August, 2011 has shown that the unique features of this new *Arctotis* plant are stable and reproduced true to type in successive generations.

SUMMARY OF THE INVENTION

Plants of the new *Arctotis* plant have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Bonarc 1116'. These characteristics in combination distinguish 'Bonarc 1116' as a new and distinct *Arctotis* plant:

1. Compact and semi-upright plant habit.
2. Freely branching growth habit.
3. Relatively small leaves.
4. Freely flowering habit.
5. Single-type inflorescences with dark pink-colored ray florets.
6. Good garden performance.

Plants of the new *Arctotis* differ from plants of the female parent selection in the following characteristics:

1. Plants of the new *Arctotis* are more compact than and not as vigorous as plants of the female parent selection.
2. Plants of the new *Arctotis* and the female parent selection differ in ray floret color as plants of the female parent selection have dark orange-colored ray florets.

Plants of the new *Arctotis* differ from plants of the male parent selection in the following characteristics:

1. Plants of the new *Arctotis* are denser than and not as open as plants of the male parent selection.
2. Plants of the new *Arctotis* and the male parent selection differ in ray floret color as plants of the male parent selection have light pink-colored ray florets.

Plants of the new *Arctotis* can be compared to plants of *Arctotis hybrida* 'Archnah', disclosed in U.S. Plant Pat. No. 14,732. In side-by-side comparisons, plants of the new *Arctotis* differ primarily from plants of 'Archnah' in the following characteristics:

1. Plants of the new *Arctotis* are more compact than and not as mounding as plants of 'Archnah'.
2. Plants of the new *Arctotis* and 'Archnah' differ in ray floret color as ray florets of 'Archnah' have orange-colored ray florets.

BRIEF DESCRIPTION OF THE PHOTOGRAPHS

The accompanying photographs illustrate the overall appearance of the new *Arctotis* plant. These photographs show the colors as true as it is reasonably possible to obtain in colored reproductions of this type. Colors in the photographs may differ slightly from the color values cited in the detailed botanical description which accurately describe the colors of the new *Arctotis* plant.

The photograph at the top of the sheet is a side perspective view of a typical flowering plant of 'Bonarc 1116' grown in a container.

The photograph at the bottom of the sheet is a close-up view of a typical inflorescence of 'Bonarc 1116'.

DETAILED BOTANICAL DESCRIPTION

The aforementioned photographs and following observations, measurements and values describe plants grown during the spring in 20-cm containers in an outdoor nursery in Higashiomi, Shiga, Japan and under cultural practices typical of commercial *Arctotis* production. During the production of the plants, day temperatures ranged from 20° C. to 30° C. and night temperatures ranged from 13° C. to 25° C. Plants were three months old when the photographs were taken and four months old when the detailed description was taken. In the following description, color references are made to The Royal Horticultural Society Colour Chart, 2007 Edition, except where general terms of ordinary dictionary significance are used.

Botanical classification: *Arctotis hybrida* 'Bonarc 1116'.

Parentage:

*Female, or seed, parent*.—Proprietary selection of *Arctotis hybrida* identified as code number 09-74, not patented.

*Male, or pollen, parent*.—Proprietary selection of *Arctotis hybrida* identified as code number 09-1, not patented.

Propagation:

*Type*.—Vegetative tip cuttings.

*Time to initiate roots, summer*.—About ten days at temperatures about 20° C. to 25° C.

*Time to initiate roots, winter*.—About 17 days at temperatures about 20° C. to 25° C.

*Time to produce a rooted young plants, summer*.—About three weeks at temperatures about 20° C. to 25° C.

*Time to produce a rooted young plants, winter*.—About four weeks at temperatures about 20° C. to 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous single-type potted *Arctotis* plant; compact and semi-upright plant habit; vigorous growth habit; freely branching growth habit with numerous lateral branches developing per plant; dense and bushy appearance.

*Plant height, to top of inflorescences*.—About 19.8 cm.

*Plant width*.—About 30.5 cm.

*Lateral branches*.—Length: About 12.4 cm. Diameter: About 3.6 mm. Internode length: About 3.5 cm. Strength: Strong. Aspect: Upright to slightly outwardly. Texture: Tomentose and pubescent. Color: Close to 141D.

Leaf description:

*Arrangement*.—Alternate, simple.

*Length*.—About 6.9 cm.

*Width*.—About 2.7 cm.

*Shape*.—Roughly elliptic, pinnatifid.

*Apex*.—Acute.

*Base*.—Cuneate.

*Margin*.—Dentate.

*Texture, upper and lower surfaces*.—Tomentose and pubescent.

*Venation pattern*.—Pinnate, reticulate.

*Color*.—Developing leaves, upper surface: Close to N137B. Developing leaves, lower surface: Close to N137C. Fully expanded leaves, upper surface: Close to N137B; venation, close to 145A. Fully expanded leaves, lower surface: Close to 137C; venation, close to 143C.

*Petiole length*.—About 3.9 cm.

*Petiole diameter*.—About 2.2 mm.

*Petiole texture, upper and lower surfaces*.—Pubescent.

*Petiole color, upper surface*.—Close to N144D.

*Petiole color, lower surface*.—Close to 144A.

Inflorescence description:

*Appearance*.—Single-type (daisy) inflorescence form with lanceolate-shaped ray florets and tubular disc florets; inflorescences borne on terminal and axillary peduncles above the foliar plane; ray and disc florets arranged acropetally on a capitulum; inflorescences face mostly upright.

*Fragrance*.—None detected.

*Flowering season*.—Plants flower during the spring and again in the autumn in Japan; plants begin flowering about six to eight weeks after planting.

*Inflorescence longevity*.—Inflorescences last about seven to ten days on the plant; inflorescences persistent.

*Quantity of inflorescences*.—Freely flowering habit with about 38 inflorescences developing per plant.

*Inflorescence buds*.—Height: About 1.2 cm. Diameter: About 1.2 cm. Shape: Ovoid. Color: Close to 71A.

*Inflorescence size*.—Diameter: About 6.4 cm. Depth (height): About 2.6 cm. Diameter of disc: About 1.4 cm. Receptacle diameter: About 8.8 mm. Receptacle height: About 2.8 mm.

*Ray florets*.—Quantity and arrangement: About 21 ray florets arranged in a single whorl. Length: About 2.8 cm. Width: About 7.3 mm. Shape: Lanceolate. Apex: Acute and shallowly emarginate. Base: Attenuate. Margin: Entire. Orientation: Initially upright, then perpendicular to the peduncle; apices slightly reflexed. Texture, upper and lower surfaces: Smooth, glabrous; satiny. Color: When opening, upper surface: Close to 71B. When opening, lower surface: Close to 70C. Fully opened, upper surface: Close to 71C; towards the base, close to NN155B; venation, close to 71A; color becoming closer to 75A with development. Fully opened, lower surface: Close to 69B; vcnation, close to 71A.

*Disc florets*.—Quantity and arrangement: About 149 massed at center of the receptacle. Length: About 5.6 mm. Diameter, at base: About 1 mm. Shape: Tubular, elongated. Apex: Five-pointed. Color, immature: Close to 202A. Color, mature: Close to 152A.

*Phyllaries*.—Quantity and arrangement: About 34 arranged in about five imbricate whorls. Length, outer phyllaries: About 5.5 mm to 7 mm. Width, outer phyllaries: About 1.8 mm to 2.7 mm. Length, center phyllaries: About 7.2 mm. Width, center phyllaries: About 5 mm. Length, inner phyllaries: About 8.5 mm to 11 mm. Width, inner phyllaries: About 5.6 mm to 6 mm. Shape, outer phyllaries: Narrowly deltoid. Apex, outer phyllaries: Acute. Shape, center phyllaries: Deltoid to ovate. Apex, center phyllaries: Acute. Shape, inner phyllaries: Ovate to obovate. Apex, inner phyllaries: Obtuse to rounded. Base, outer, center and inner phyllaries: Fused. Margin, outer, center and inner phyllaries: Entire. Texture, outer and center phyllaries: Pubescent. Texture, inner phyllaries: Smooth, glabrous. Color, outer and center phyllaries, upper and lower surfaces: Close to 141A; towards the margins, tinged with close to N79C. Color, inner phyllaries, upper and lower surfaces: Close to 143C; center and towards the apex, tinged with close to N79C.

*Peduncles*.—Length: About 10.8 cm. Diameter: About 2.3 mm. Angle: Upright to slightly outwardly. Strength: Strong, flexible. Texture: Tomentose and pubescent; rough. Color: Close to 144C.

*Reproductive organs*.—Androecium: Quantity per disc floret: Five. Stamen length: About 4.4 mm. Anther size: About 1.9 mm by 0.9 mm. Anther shape: Lanceolate. Anther color: Close to N79A. Pollen amount: Scarce. Pollen color: Close to 13A. Gynoecium: Quantity per ray and disc florets: One. Pistil length: About 5.1 mm. Stigma shape: Bi-parted. Stigma color: Close to 200A. Style color: Close to N163D. Ovary color: Close to 155B.

*Seeds and fruits*.—Seed and fruit production has not been observed on plants of the new *Arctotis*.

Pathogen & pest resistance: Plants of the new *Arctotis* have not been observed to be resistant to pathogens and pests common to *Arctotis* plants.

Garden performance: Plants of the new *Arctotis* have been observed to have good garden performance and to tolerate wind, rain and temperatures ranging from about 0° C. to about 40° C.

It is claimed:

1. A new and distinct *Arctotis* plant named 'Bonarc 1116' as illustrated and described.

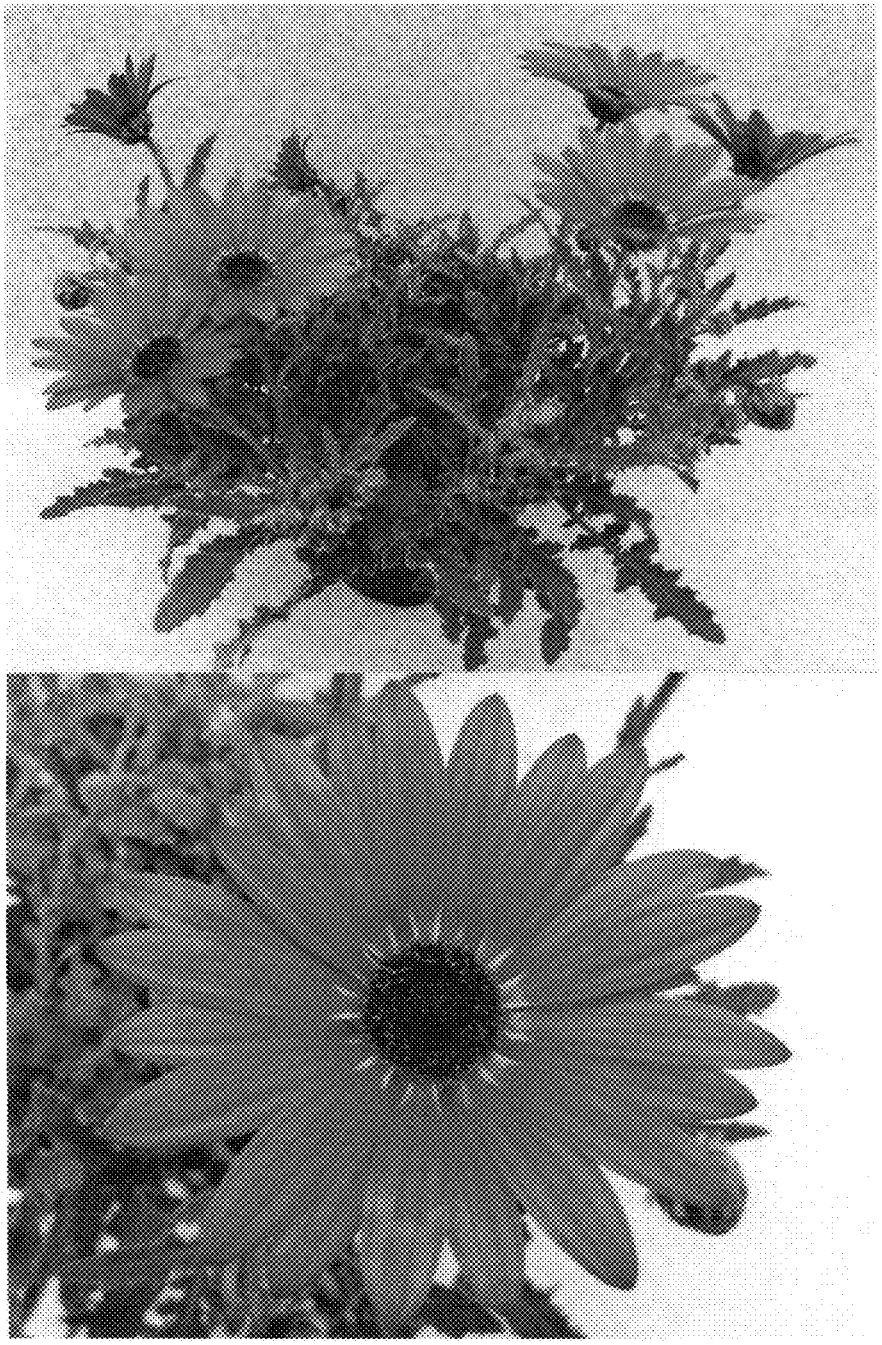

* * * * *